(12) United States Patent
Migliorato et al.

(10) Patent No.: US 6,657,269 B2
(45) Date of Patent: Dec. 2, 2003

(54) SENSOR CELL

(75) Inventors: Piero Migliorato, Cambridge (GB);
Nathan Bavidge, Cambridge (GB);
Christopher Lowe, Cambridge (GB)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 10/022,232

(22) Filed: Dec. 20, 2001

(65) Prior Publication Data

US 2002/0117694 A1 Aug. 29, 2002

(30) Foreign Application Priority Data

Dec. 22, 2000 (GB) .............................................. 0031716

(51) Int. Cl.⁷ ............................................... H01L 29/84
(52) U.S. Cl. ......................................... 257/414; 257/71
(58) Field of Search ................................. 257/414, 71

(56) References Cited

U.S. PATENT DOCUMENTS

| | | | |
|---|---|---|---|
| 4,968,400 A | * 11/1990 | Shimomura et al. ... | 204/403.11 |
| 5,719,033 A | * 2/1998 | Ackley et al. ............... | 204/400 |
| 5,827,482 A | 10/1998 | Shieh et al. | |
| 6,111,280 A | * 8/2000 | Gardner et al. ............. | 257/253 |
| 6,200,444 B1 | * 3/2001 | Ahlers et al. ............... | 204/416 |
| 6,411,727 B1 | * 6/2002 | Harkin ....................... | 340/5.83 |

FOREIGN PATENT DOCUMENTS

| | | |
|---|---|---|
| EP | 0 751 392 A2 | 1/1997 |
| EP | 0 908 725 A1 | 4/1999 |
| EP | 1 041 356 A1 | 10/2000 |
| WO | WO 89/09932 | 10/1989 |
| WO | WO 97/39145 | 10/1997 |

* cited by examiner

Primary Examiner—Jerome Jackson
(74) Attorney, Agent, or Firm—Oliff & Berridge, PLC

(57) ABSTRACT

A sensor cell comprises receiving means, which may be in the form of an electrode 10 coupled to the gate electrode of a thin film transistor T1. In one form of the invention a voltage supplied to the gate electrode of the transistor T1 via a switching transistor T7 is controlled in dependence upon the value of capacitance $C_A$ arising at the electrode from receipt of a sample for identification. Thus, the operation of transistor T1 can be used to identify the sample received by the electrode 10.

49 Claims, 6 Drawing Sheets

Steady-State Detection

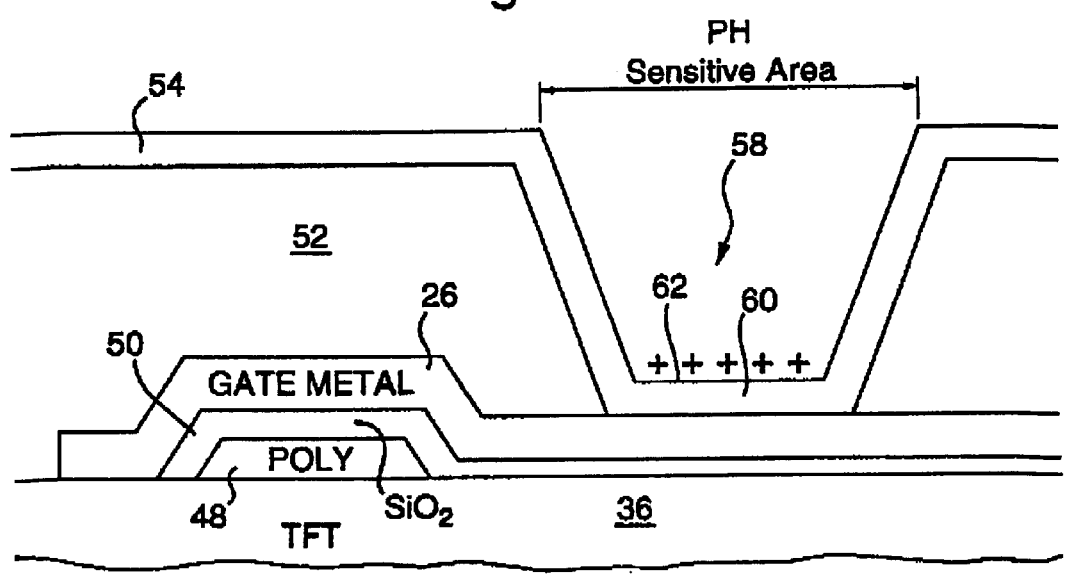

SENSOR CELL

BACKGROUND OF THE INVENTION

1. Field of Invention

The present invention relates to sensor cells and to sensors which incorporate such sensor cells.

2. Description of Related Art

Chemical sensors incorporating arrays of sensor cells including semiconductor transistors are known. Such sensors have typically used a silicon wafer as the substrate material. However, silicon is a relatively expensive material. Furthermore for certain types of sensors, such as biosensors, disposability of the sensor after use is an especially important issue as the biosensor can only be used once before disposal. When silicon is used as the substrate material, disposing of the used biosensors becomes more problematical.

Additionally, the difficulties associated with fabricating transistor arrays on silicon substrates are known to increase significantly with increase in the size of the array. Hence, with silicon substrates the tendency is for a high density of devices for any given size of array. For biosensors, this high packing density can be problematical because for many applications the active parts of the microelectronic chip incorporating the array must operate in a wet environment.

Many forms of chemical sensors, such as biosensors, have been proposed. One type of multi-biosensor comprises a pH sensor in the form of an array of four Ion Sensitive Field Effect Transistors (ISFET's) in Urination with four Metal Oxide Silicon Field Effect Transistors (MOSPET's) acting as source follower circuits. However, in order to provide sufficient isolation between the ISFET's, the proposed array was relatively bully in size. Furthermore, an IFSET is a form of transistor and considerable problems arise in isolating such devices from a solution being tested. To alleviate the problems of isolation, the ISFET's and MOSFET's have been proposed to be fabricated on a silicon layer in the form of a number of discrete sites supported on a sapphire substrate. Sapphire was used as the substrate material because of its excellent electrical isolation properties. A protectional membrane was then formed over the gate surfaces of the ISFET's, followed by membranes respectively sensitive to the compounds to be tested. The individual sensors so produced functioned as pH sensors and could be used to detect urea, glucose and potassium. However, as mentioned above, the sensor array was of relatively large size, measuring approximately 2 mm in width and 6 mm in length for a four sensor array. Furthermore, sapphire substrates can only be used to fabricate arrays to a certain size and it is well known that the concerns rating to the fabrication of arrays using silicon increase significantly with increase of array size. Additionally, the silicon and, in particular, the sapphire substrate materials are relatively expensive and therefore chemical sensors of the above type are extremely costly to fabricate. This cost aspect is particularly burdensome when considering that many types of sensors can only be used once before disposal. Moreover, these materials are not readily disposable, giving rise to significant environmental concerns regarding disposal after use.

More recently, sub-micron CMOS technology has been proposed for use as a biosensor array for DNA analysis. This technology has enabled an array of up to about 1000 sensor cells to be fabricated on a substrate having a size in the order of a few millimeters square. However, as the CMOS devices are fabricated on a silicon substrate, the proposed array has a high packing density. To isolate the active CMOS devices from the wet operating environment, a specific integrated reaction test chamber is provided in the form of a cavity arranged between two superimposed and hermetically sealed primed circuits. The DNA material to be analysed is separated into its two strands by heating and, using a biochemical process, the stands are labelled with a fluorescent molecule. An analyte containing the DNA strands is then placed in contact with the chip. If a DNA strand has a sequence matching that of a target arranged on an electrode of the sensor, hybridisation occurs which results in a physical localisation of the DNA sample onto the appropriate electrode of the chip. The chip is then rinsed and the sensor is read with a CCD camera. As the DNA strands have been labelled with a fluorescent molecule, relative brightness on the electrodes of the device indicates where bonding has occurred. Key issues in the applicability of such devices are recognised as materials compatibility, manufacturing and packaging in order to reliably deliver a wet-chip concept and these can be compromised by the requirement to achieve a high packaging density on the silicon substrate material. Also, as will be apparent from the above description, such biosensors are relatively expensive to manufacture.

Thin film transistors (TFT's) are relatively inexpensive to manufacture as relatively cheap non-silicon substrates such as soda glass or plastic can be used. The use of a plastics substrate can provide additional benefits as it is a relatively disposable material. Furthermore, TFT's can be readily fabricated as large area arrays and such technology has already found widespread application in industry, such as for example, in the manufacture of active matrix liquid crystal display devices. The manufacturing processes are therefore well proven and a high yield of operable devices can reliably be obtained at relatively low costs, especially in comparison to silicon substrate devices. These advantages are further enhanced when considering that arrays larger than those available from silicon substrates can also be reliably fabricated. The use of silicon wafer substrates for such large area arrays is considered to be extremely problematical as it becomes increasingly difficult and expensive to fabricate the arrays in view of the substrate material itself and the semiconductor fabrication techniques which must necessarily be employed.

There are also drawbacks associated with the performance of such devices when used to sense certain substances. MOSFET's typically comprise a relatively thin layer of silicon dioxide ($SiO_2$) supported on a doped silicon substrate. The $SiO_2$ layer has inherent capacitance which is inversely proportional to the thickness of the layer. If the $SiO_2$ layer is fabricated to a typical thickness of about 100 nm, there is significant loss of capacitive signal from the device which is due to the inherent capacitance of the $SiO_2$ layer. If the $SiO_2$ layer is fabricated as a very thin layer to improve signal output, the devices become very unstable in use. These design conflicts can be alleviated if the sensing electrode is made very small. However, the sensing electrode must be fabricated to a practical size as it is used to receive the substance being identified. The MOSFET gate area must therefore be mad relatively large but this gives rise to the basic fabrication concern regarding the use of silicon transistors for chemical sensors in that the provision of relatively large gate areas significantly reduces the packing density of the transistors which can be accommodated on the finite size silicon substrates, which in turn reduces the number of sensor cells that can be accommodated in the sensor array.

SUMMARY OF THE INVENTION

For chemical or biosensors in particular, the ability of TFT's to be readily fabricated as large area arrays at relatively low cost presents significant advantages in comparison to the conventionally used silicon devices as the need to achieve a very high packing density is not a dominant factor in device design. Hence, the area associated with each sensor cell of an array which receives the sample to be identified can, if necessary, be displaced from the active semiconductor components, alleviating the isolation concerns which exist with the current silicon substrate devices. Furthermore, the sensing areas for receiving a sample to be identified, which may be in the form of electrodes for a DNA sensor, can be made relatively large in size, enlarging the sensing area and enhancing device performance. Additionally, the use of enlarged sensing areas can provide a further benefit in that the packing density of the TFT's can be reduced from that found in many current applications where these devices are used providing increased yields of fully functional devices from the existing fabrication processes.

TFT's are known to exhibit lower mobility than silicon substrate transistors and, when fabricated as a large array of transistor devices, which would be of particular benefit for a biosensor, TFT's can exhibit variations in transfer characteristic between the transistors in the array. These variations can become more pronounced as the array size is increased and for DNA biosensors in particular, where typically a very large number of samples need to be analysed to identify a sample, a large area array is of very significant benefit in reducing the time required to analyse samples.

Hence, it has been further realised with a preferred form of the present invention that, if the capacitance arising between an electrode and a sample to be identified is used as a measurement technique, the potential drawbacks associated with the variability in TFT performance can be overcome, enabling such devices to be readily used as the active devices for a chemical sensor in the form of a large array of sensor cells.

The use of TFT's for chemical sensors not only provides the cost benefit over the use of silicon substrate devices but also provides the ability to fabricate large area arrays with enhanced sensing areas. Furthermore, there is also the significant additional benefit of improved disposability, which is particularly important for biosensor or chemical sensor devices because, as stated above, such devices can usually be used once only before disposal.

It is therefore an object of the present invention to provide an improved sensor cell utilising thin film transistors. Furthermore, it is also an object of the present invention in which detection of the capacitance on an electrode arising from the electrode receiving a sample for identification is used as the measurement technique and this capacitance is used to control the operation of the thin film transistors.

According to a first aspect of the present invention, there is provided a sensor cell comprising a thin film transistor and receiving means coupled to a gate electrode of the thin film transistor for receiving a sample for identification.

In a preferred arrangement, the sensor cell comprises a reference capacitor and the sample electrode and the reference capacitor are arranged as a capacitance divider circuit coupled to a gate electrode of the thin film transistor for controlling the amplitude of a voltage pulse provided to the gate electrode in dependence upon the value of capacitance arising at the sample electrode.

In an advantageous structure for the sensor cell, the reference capacitor comprises the gate electrode and a buried region underlying the gate electrode and separated therefrom by an insulator layer.

Preferably, the receiving means comprises a sample electrode, the arrangement being such that operation of the thin film transistor is controlled in dependence upon a value of capacitance arising at the sample electrode in response to receipt by the sample electrode of the sample for identification.

In an alternative arrangement, the sensor cell comprises a switching transistor for switching between a conducting condition and a non-conducting condition and wherein the thin film transistor includes a gate electrode, the arrangement being such that a voltage provided to the gate electrode with the switching transistor in the conducting condition reduces in magnitude in dependence upon the value of the capacitance arising at the sample electrode when the switching transistor is switched to the non-conducting condition.

Preferably, in this first aspect of the present invention, the sensor cell comprises a select line for providing a select pulse for switching the switching transistor between the conducting and non-conducting conditions and a write line for providing the voltage to the gate electrode of the thin film transistor, a read line for providing a read voltage to the thin film transistor, the arrangement being such that a write cycle is enabled by providing the select pulse to the switching transistor, thereby to switch the switching transistor to a conducting condition to enable the voltage to be provided to the control gate of the thin film transistor, and wherein a read cycle is enabled by terminating the select pulse thereby to switch the switching transistor to the non-conducting condition, whereby the voltage at the gate electrode of the thin film transistor changes in magnitude, thereby to switch the thin film transistor to a non-conducting condition for terminating the provision of an output signal from the thin film transistor, the time taken between termination of the select pulse and switching of the thin film transistor to the non-conducting condition being dependent upon the value of capacitance at the sample electrode.

Advantageously, the sensor cell may include a threshold voltage compensation circuit including a constant current source for providing a preset level of current through the film transistor and switching means for selectively coupling the constant current source to the thin film transistor.

Most advantageously, the sensor cell comprises an additional transistor coupled to the thin film transistor, the arrangement being such that when the voltage pulse is provided to the gate electrode of the thin film transistor and tie constant current source is decoupled from the thin film transistor, the magnitude of the output current from the thin film transistor will change from a first level determined by the constant current source to a second level in dependence upon the value of capacitance arising at the sample electrode Advantageously, the receiving means is arranged in a position offset from the thin film transistor, the arrangement being such that the sample is received by the receiving means in a position which does not overlie the gate region of the thin film transistor.

Preferably, the sensor cell is fabricated on a plastics substrate.

According to a second aspect of the present invention there is provided a sensor comprising an array of rows and columns of sensor cells in accordance with the first aspect of the present invention.

According to a third aspect of the present invention there is provided a method for identifying a sample comprising providing a sensor cell including a thin film transistor and a sample electrode for receiving the sample and controlling the operation of the thin film transistor in dependence upon a value of capacitance arising at the sample electrode from receipt by the sample electrode of the sample.

Preferably, the method comprises providing a reference capacitor and arranging the reference capacitor and the sample electrode as a capacitance divider circuit coupled to the gate electrode of the thin film transistor and controlling the amplitude of a voltage pulse afforded to the gate electrode in dependence upon the value of capacitance arising at the sample electrode.

Advantageously, in this second aspect of the present invention the method comprises coupling the sample electrode with a switching transistor for switching between a conducting condition and a non-conducting condition, providing a voltage to a gate electrode of the thin film transistor with the switching transistor in the conducting condition, and coupling the sample electrode to the switching transistor whereby when the switching transistor is switch to the nonconducting condition the voltage provided to the gate electrode of tie thin film transistor changes in magnitude in dependence upon the vale of the capacitance arising at the sample electrode.

Preferably, the switching transistor is switched between the nonconducting and conducing conditions by providing a select pulse from a select line to the switching transistor and a write line is provided for providing the voltage to the gate electrode of the thin film transistors a read line for providing a read voltage to the thin film transistor, enabling a write cycle by providing the select pulse to the switching transistor, thereby to switch the switching transistor to a conducting condition to provide the voltage to the control gate of the tin film transistor, and enabling a read cycle by terminating the select pulse thereby to switch the switching transistor to the non-conducting condition, whereby the voltage at the gate electrode of the thin film transistor changes in magnitude, thereby to switch the thin film transistor to a nonconducting condition and terminate an output signal from the thin film transistor, the time taken between the termination of the select pulse and switching of the thin film transistor to the nonconducting condition beg dependent upon the value of capacitance at the sample electrode.

Most preferably, the method comprises providing the thin film transistor on a plastics substrate.

Advantageously, the method also comprises coupling an additional transistor to the thin film transistor, providing the voltage pulse to the gate electrode of the thin film transistor and decoupling the constant current source from the thin film transistor thereby to change the magnitude of the output current from the thin film transistor from a first level determined by the constant current source to a second level in dependence upon the value of capacitance arising at the sample electrode.

According to a fourth aspect of the present invention, there is provided a biosensor comprising a sensor cell according to the first aspect of the present invention or a sensor according to the second aspect of the present invention.

According to a fifth aspect of the present invention, there is provided fingerprint recognition apparatus comprising a sensor cell according to the first aspect of the present invention or a sensor according to the second aspect of the present invention.

According to a sixth aspect of the present invention, there is provided a method of operating a biosensor or fingerprint recognition apparatus according to the third aspect of the present invention.

BRIEF DESCRIPTION OF THE DRAWINGS

The present invention will now be described, by way of further example only, with reference to the accompanying drawings in which:

FIG. 7 illustrates an alternative s cure for a sensor cell for use as a pH sensor in accordance with the present invention.

DETAILED DESCRIPTION OF PREFERRED EMBODIMENTS

Figure 1:
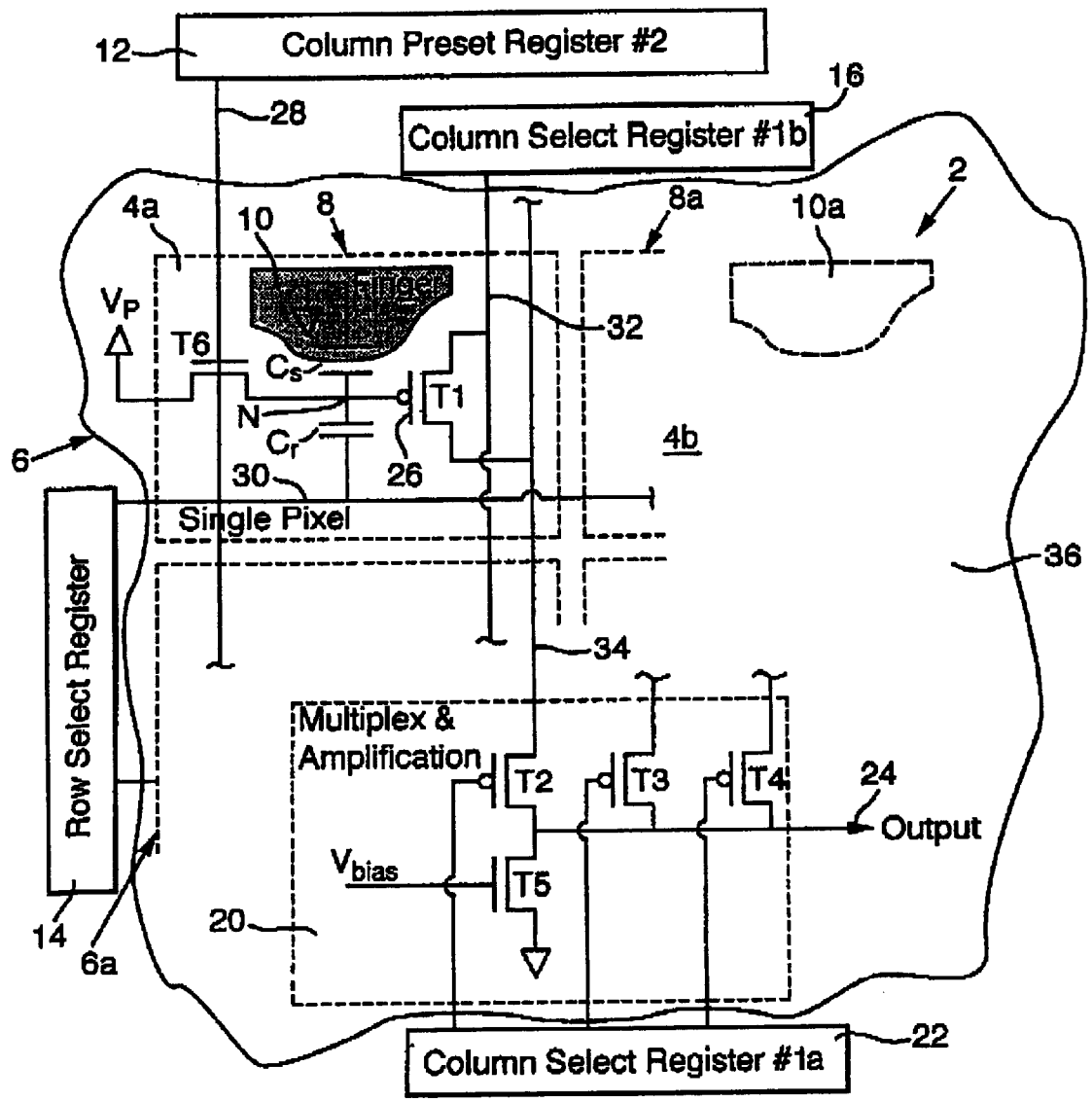
FIG. 1 illustrates a sensor according to a first embodiment of the present invention.

Referring to FIG. 1, a sensor 2, such as a chemical sensor, comprises an array of sensor cells 4a, 4b . . . 4n, arranged in rows 6, 6a . . . 6n and columns 8, 8a . . . 8n. Each sensor cell 4a includes a thin film transistor (TFT), T1, an electrode 10, a further transistor T6 and a reference capacitor Cr. The sensor 2 also includes a column preset register 12, a row select register 14, and a column select register 16, the function of which is described below. Multiplex and amplification circuit 20, operating under the control of a second column select register 22, is also provided for amplifying and multiplexing output signals from the sensor cells to provide an output signal from the sensor array on output line 24. In FIG. 1, the electrode 10 is shown as a plate electrode for receiving a finger tip, but, equally, the electrode 10 could comprise an electrode in solution. Each of the sensor cells of the array has a circuit configured as the sensor cell 4a shown in FIG. 1.

The sensor shown in FIG. 1 operates in a steady state detection mode with the voltage on the gate electrode 26 of transistor T1 being determined by the value of the capacitance arising on the electrode 10 (denoted by the capacitor symbol Cs in FIG. 1) resulting from the electrode 10 receiving a sample for identification, in combination with the value of the reference capacitor Cr.

At the start of a cycle, the sensor cells in a column, for example column 8, are preset by the application of a voltage from the column preset register 12 on preset line 28. The transistor T6 of each cell is turned ON and a bias voltage Vp is applied to the gate electrode 26 of transistor T1. The bias voltage Vp is provided so that transistor T1 is set to a known operating point on its characteristic and is ready to switch from a non-conducting to a conducting condition. It also ensures that the voltage at the gate electrode 26, when a subsequent pulse is applied thereto, as is described below, does not rise to a level which would cause too high a current to be passed by transistor T1, possibly destroying transistor T1.

The row select register 14 is used to provide row select pulses on line 30 to the node N via the reference capacitor Cr. The column select register 16 is used to supply a column select pulse on line 32. The row select and column select pulses are only supplied to one row and one column at any point in time, enabling a single cell, such as the sensor cell 4a in FIG. 1, to be selected. Assuming, for example, that a fingertip whose fingerprint is to be identified is being received by the sensor 4a. A part of the fingertip will be received by the electrode 10 and an adjacent part of the fingertip will be received by electrode 10a of the immediately adjacent sensor cell 4b in column 8a. The fingertip surface acts a co-operating electrode to the electrodes 10 and 10a, and hence a value of capacitance, denoted as Cs in FIG. 1, can be read between the fingertip and each of the electrodes 10 and 10a. The capacitances Cs and Cr create in effect an AC potential divider and hence, when the sensor cell 4a receives the row select pulse on line 30, the magnitude of the voltage at node N will vary in dependence upon the value of the reference capacitance Cr and the value of the capacitance Cs arising from the fingertip on the electrode 10.

As stated above, transistor T1 is biased almost to the point of conduction by the application of the voltage Vp to the gate electrode 26. Hence, when the sensor cell 4a is selected by the application of a row select pulse on line 30 and a column select pulse on line 32, the magnitude of the voltage at node P, initially at value Vp, will increase to a value determined by the relative values of the capacitances Cs and Cr. Because Cr is a fixed reference value capacitor, the value of this voltage will be proportional to the value of capacitance Cs. It follows that the value of the output current from transistor T1 will also be proportional to the value of capacitance Cs. The tin film transistor T1 is, therefore, being controlled in dependence upon the value of the capacitance arising at the sample electrode 10 resulting from the receipt by the sample electrode of the sample to be identified, i.e. a portion of the fingerprint on the fingertip.

The current on output line 34 is fed to the multiplex and amplification circuit 20. In the multiplex and amplification circuit 20, a transistor T1 is provided with a select signal from the second column select register 22 simultaneously with the column select signal on line 32. A bias voltage $V_{bias}$ is provided to the gate electrode of transistor T5. In this manner the output current on line 34 can be amplified and multiplexed onto output 24 by appropriate selection of transistor T1. Likewise, the output current from other sensor cells can also be multiplexed onto output 24.

It will be appreciated that in the case when the sensor 2 comprises fingerprint recognition apparatus, a fingertip placed into contact with the sensor will have ridges of the fingerprint pattern in contact with certain sample electrodes and troughs of the fingerprint pattern in contact with other sample electrodes. Assuming that a fingerprint ridge is received by electrode 10 and a fingerprint trough is received by electrode 10a, the value of capacitance Cs for the sensor cell 4a will differ from the value of capacitance Cs for the sensor cell 4b. The same applies for other sensor cells in the array receiving ridge or trough portions of the fingerprint pattern. Typically, the sensor 4 may comprise a 200×300 sensor cell array. Hence, with appropriate timing of the signals from the row select register 14, and column select registers 16 and 22, the sensor cells of the array can be sequentially scanned and the multiplexed output signals of the sensor cells appearing on output 24 can be fed to a store. A comparator may compare the stored values for the samples with reference values and, as a result of such comparison, the fingerprint may be identified. The output signals on output 24 may also be fed to a display for displaying an image of the fingerprint as sensed by the sensor 2.

Preferably the multiplex and amplification circuit 20 is fabricated integrally with the sensor 2, in which case the transistors of the circuit, of which transistors T1 to T5 are shown, may also comprise TFT's on a common substrate 36 with the sensor 2. The transistor T6 for each sensor cell may also comprise a TFT. The substrate 36 may comprise any suitable support material but, advantageously, if all of the transistors of the sensor 2 are fabricated as TFT's, the substrate 36 may preferably comprise plastics material.

Although the steady state detection sensor shown in FIG. 1 has been described with reference to a fingerprint recognition apparatus, it may also be used as a biosensor to detect or recognise biomaterials in solution, such as DNA or antibodies. In this case, a number of electrodes are provided which receive the substance in solution. The values of capacitance arising from the substance can be compared with known reference values in order to identify the particular substance.

Figure 2:
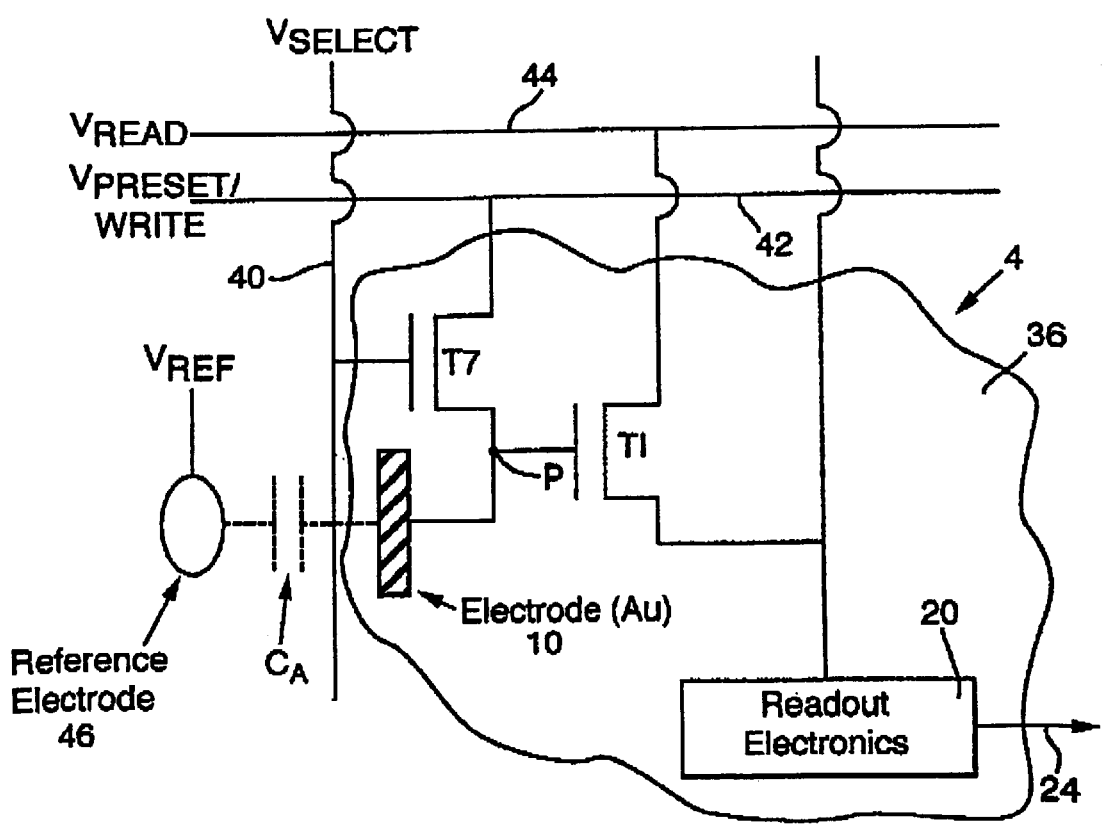
FIG. 2 illustrates a sensor according to a second embodiment of the present invention.

FIG. 2 shows an alternative embodiment for a sensor cell in accordance with the present invention. The sensor cell shown in FIG. 2 operates in a 'transient detection' mode in which a time constant determined by, for example, the value of capacitance arising from an electrode receiving a DNA sample for identification, is used to identify the sample.

In the sensor cell 4 shown in FIG. 2, a switching transistor T7 is coupled to the electrode 10 and a node P provided between the transistor T7 and electrode 10 is coupled to the gate electrode of the thin film transistor T1. Select line 40, write line 42, and read line 44 are provided for respectively providing select signal $V_{select}$, preset signal $V_{preset}$ and read signal $V_{read}$. A multiplex and amplifier circuit 20 is provided for providing an output signal on output 24.

Operation of the circuit shown in FIG. 2 will be described with reference to identification of a DNA sample in solution. However, it should be understood that the transient detection circuit shown in FIG. 2 can also be used for fingerprint recognition, in a similar manner to that described with reference to FIG. 1. In the case of fingerprint detection, reference electrode 46 of FIG. 2 would be constituted by the surface of the fingertip and the voltage $V_{ref}$ of FIG. 2 would be provided by the charge occurring on the surface of the fingertip.

At the start of an operas cycle the transistors T1 and T7, which may both comprise TFT's, are in a non-conducting or OFF condition. The electrode 10 is arranged as an electrode in a suitable reservoir into which is placed the DNA in solution. The DNA can be immobilised and is therefore received by the electrode 10 and, as a result, a capacitance value $C_A$ arises between the sample electrode 10 and the reference electrode 46.

A preset cycle is initiated in which the switching transistor T7 is switched from a non-conducting condition to a conducting condition by the application of the voltage $V_{select}$ to the gate electrode of transistor T7. Simultaneously, the preset voltage $V_{preset}$ is afforded to the source electrode of transistor T7 and the read voltage $V_{read}$ is afforded to the source electrode of transistor T1. When transistor T7 is switched ON, the voltage at node P rises to the level of preset voltage $V_{preset}$ and when the voltage at node P exceeds the threshold voltage of transistor T1, the transistor T1 will switch ON with the current at the output of transistor T1 being a function of the voltage at node P (the gate electrode of transistor T1).

A read cycle is then initiated by terminating the select voltage $V_{select}$, causing transistor T7 to switch back to a non-conducting or OFF condition. When transistor T7 is switched OFF, the voltage on node P reduces by leaking away through transistor T7 and the rate or the time constant for this leakage to occur depends on the value of capacitance $C_A$, which is dependent upon the identity of the DNA sample received by the sample electrode 10. As the voltage at the node P reduces in magnitude, there is a related decrease in the current at the output of thin film transistor T1, which is fed to the multiplex and amplification circuit 20. When the voltage at node P reduces to below the threshold voltage of transistor T1, transistor T1 switches OFF to further reduce the current fed to the multiplex and amplifier circuit 20 to that of a leakage current flowing through transistor T1. It will be realised from the above description that transistor T7 is used as a digital switching transistor whereas the transistor T1 acts as an analogue voltage to current converter. Therefore, by monitoring the current at the output of transistor T1, which is dependent on the value of capacitance $C_A$, the identity of the sample received by the electrode 10 can be determined.

For use as a biosensor, pairs of such sensor cells, as shown in FIG. 2, may be provided, one cell of a pair acting as the sample cell and the second of the pair acting as a reference cell in which no reaction has occurred.

When the sensor cells shown in FIGS. 1 and 2 are for use as chemical or biosensors, for example a DNA sensor, the chemical or biomaterials to be identified must first be written into the cells and onto the reference electrodes. This can be regarded as a write phase for the cells and preferably occurs when the devices are fabricated. Inkjet heads may conveniently be used to deposit the chemical or biomaterials and deposition onto the electrodes may be assisted by electrodeposition in which a charge is applied to the electrode so as to attract the material being deposited to its desired deposition site.

Figure 3:
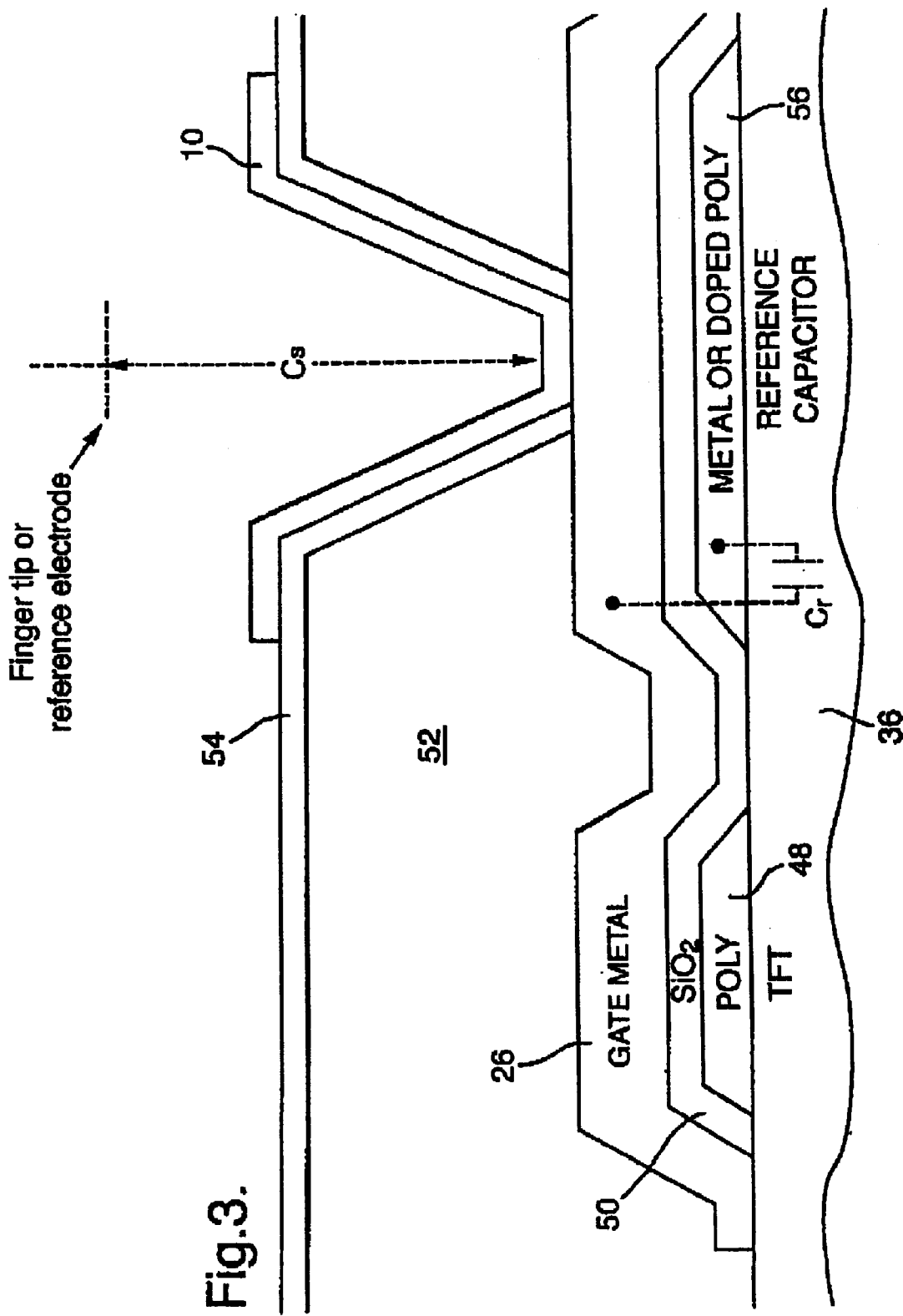
FIG. 3 illustrates a structure for a sensor cell for use in the sensor shown in FIG. 1.

FIG. 3 shows an embodiment of a semiconductor structure which may be used to provide the thin film transistor T1, the electrode 10, and the reference capacitor Cr.

The TFT structure of FIG. 3 comprises a layer of polysilicon 48 supported by the substrate 36, which preferably is of plastics or soda glass material. The gate electrode 26 is formed over the polysilicon layer 48, separated from the polysilicon layer by an insulating layer 50 of silicon dioxide. Passivation layers 52, 54 overlie the gate electrode 26.

The insulating layer 50 and the gate electrode 26 are arranged to extend beyond the region of the polysilicon layer 48 to overlie a buried region 56 of metal or doped polysilicon formed on the substrate 36. The passivation layers 52, 54 are provided with a well extending down to expose the gate electrode 26 in an area overlying the buried region 56. The electrode 10, which may comprise gold, silver or platinum, is formed in the well extending down into contact with the gate electrode 26. In this manner, the reference capacitor is provided between the buried region 56 and the gate electrode 26. For illustrative purposes, the reference capacitor is shown in phantom in FIG. 3.

Also, because the structure shown in FIG. 3 incorporates a TFT and not a silicon substrate transistor, the electrode 10 can be positioned so that it is offset from the TFT without conflicting with the need to achieve maximum packing density on the expensive silicon substrate material. The electrode 10 is therefore arranged so that it does not overlie the gate regions of the TFT. As such, the electrode 10 can be of enlarged size to improve device sensitivity but also the encapsulation required to isolate the TFT from the wet environment occurring at the electrode can be fabricated more easily and more reliably because there is no requirement to achieve a high packing density of devices on an expensive substrate.

It can be seen from FIG. 3 that the structure provides a compact arrangement incorporating the thin film transistor T1, the electrode 10, and the reference capacitor Cr. Hence, the structure can be incorporated into the steady state detection sensor cell shown in FIG. 1. When the sample to be identified is received by the electrode 10, the value of capacitance $C_s$ arising between the electrode 10 and the sample, shown diagrammatically in FIG. 3, forms in combination with the integral reference capacitor Cr, the capacitance divider circuit described with reference to FIG. 1, which controls the operation of the TFT.

For the transient detection sensor cell shown in FIG. 2, where the reference capacitor is not required, the buried region 56 can be omitted.

Figure 4:
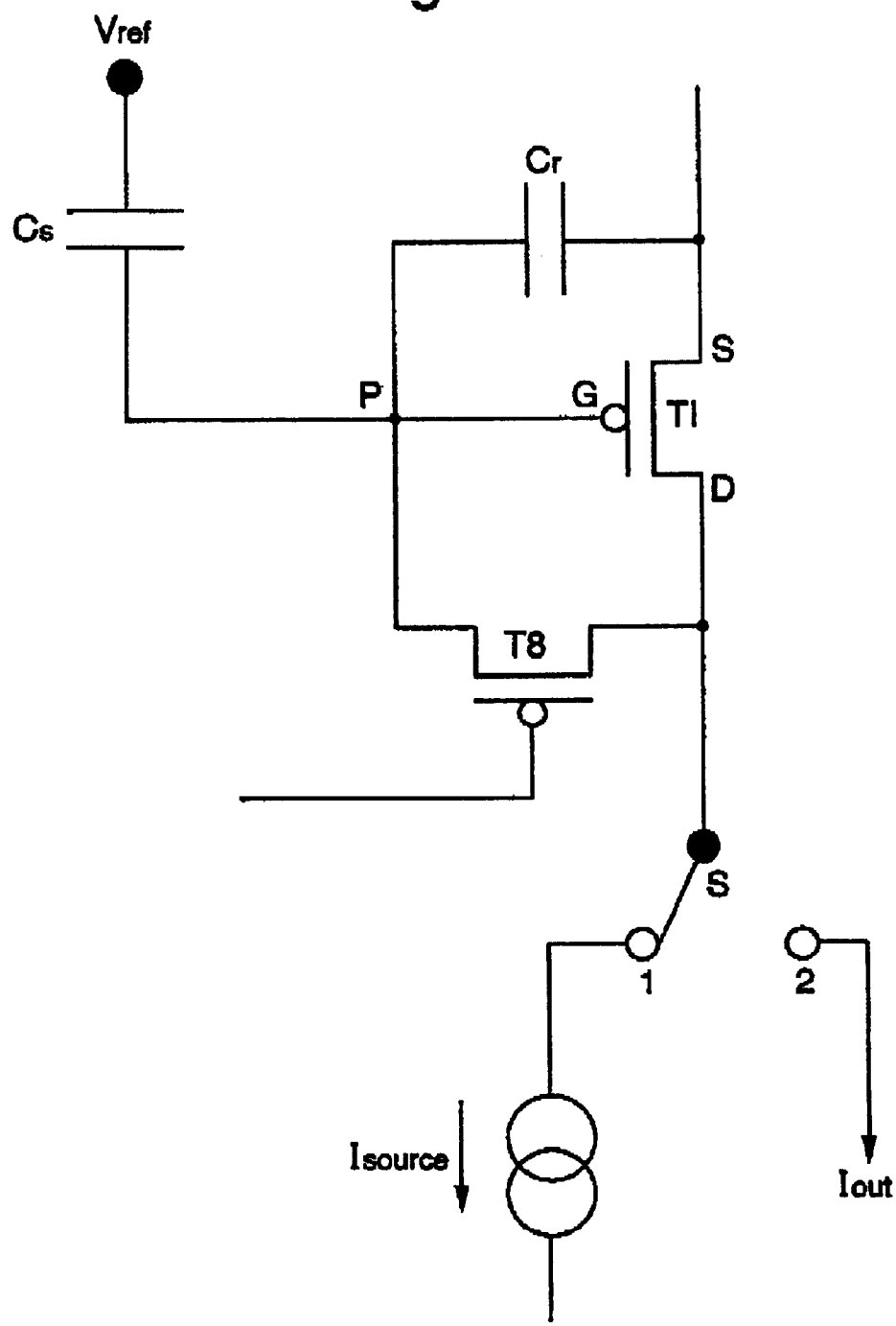
FIG. 4 illustrates a sensor cell including threshold voltage variation for use in the sensor shown in FIG. 1.

As stated above, a concern with polysilicon TFT's is threshold voltage variation. FIG. 4 illustrates an alternative circuit for a sensor cell which compensates for this variation and provides a comparable output from the TNT's across a large area substrate.

In the sensor cell of FIG. 4, the thin film transistor T1 is coupled via a switch S to either a constant current supply $I_{Source}$ or an output line. An additional transistor T8, which operates as a switching transistor, is connected between the gate and drain electrodes of thin film transistor T1, and the reference capacitor Cr is connected between the gate and source electrodes of transistor T1. The electrode for receiving the sample to be identified (not shown in FIG. 4) is also coupled to the gate electrode of transistor T1. The sample capacitance Cs forms, therefore, a capacitance divider with the reference capacitor Cr, in a similar manner to that described with reference to FIG. 1.

Figure 5:
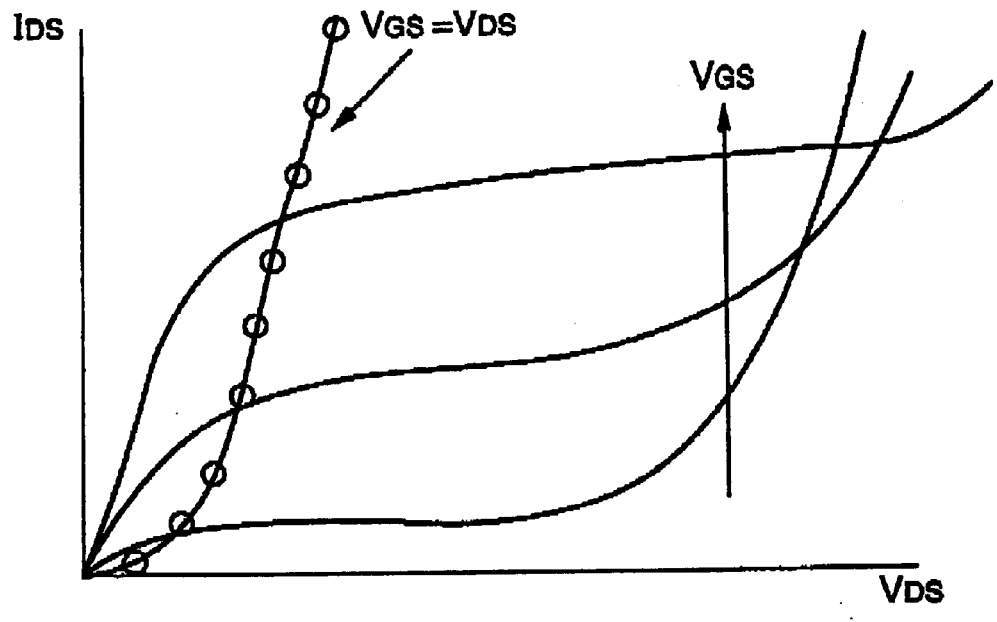
FIG. 5 illustrates a simplified operational characteristic for the thin film transistor of the sensor cell shown in FIG. 4.

When transistor T8 is turned ON, the gate to source voltage $V_{GS}$ and drain to source voltage $V_{DS}$ for transistor T1 will be equal. Under such conditions, the operational characteristic for transistor T1 is simplified, as shown in FIG. 5. With switch S in position "1", the current from the constant current source $I_{Source}$ is pulled through transistor T1, which results in a voltage drop $VD_{DSref}$ across transistor T1. Because transistor T8 is ON, (and hence $G_{GS}$ is equal to $V_{DS}$ for transistor T1), the voltage drop $V_{DSref}$ appearing across transistor T1 is stored in the reference capacitor Cr.

Figure 6:
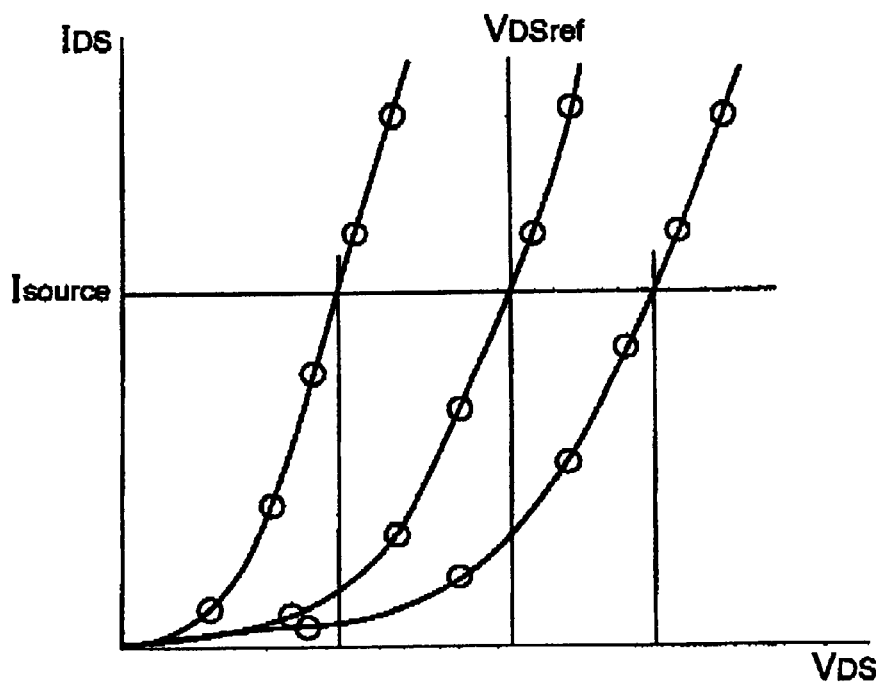
FIG. 6 illustrates the variation of the simplified operational characteristic shown in FIG. 5, with variation of the threshold voltage of the thin film transistor.

Threshold variation in thin film transistor T1 may result in a shift in the simplified operational characteristic curve (when $V_{GS}$ is equal to $V_{DS}$) for transistor T1, as shown in FIG. 6. The value of the current flowing through transistor T1 is constant as it is being supplied from the constant current source, $I_{Source}$. Any threshold variation will therefore result in a change in the voltage drop $V_{DSref}$ occurring between the source and drain electrodes of transistor T1. The voltage $V_{DSref}$ is stored in the reference capacitor Cr and, therefore, the voltage $V_{GS}$ between the gate and source electrodes of transistor T1 is precharged to this value. In this way, transistor T1 is preset to a known point on its characteristic.

If the switch S is now moved to position "2" and T8 is switched OFF, initially the current $I_{out}$ on the output line will be equal to the current from the constant current supply $I_{Source}$, as it is governed by the voltage at node P, which in turn is governed by the voltage stored on the reference capacitor Cr. If voltage source $V_{ref}$ is now pulsed, the voltage at node P increases and pulses in sympathy with the voltage $V_{ref}$. The current $I_{out}$ at the output line will also pulse in sympathy with the increase in the voltage at the node P.

The reference capacitor Cr and the capacitance Cs form a capacitive divider and, hence, the increase in the voltage at node P when the voltage source $V_{ref}$ is pulsed will be determined by the relative capacitance values of Cr and Cs. The increase in the output current $I_{out}$ from its initial value equal to the current from the constant current supply $I_{Source}$ can be measured to quantify the value of capacitance Cs, which is indicative of the sample received by the sample electrode.

It will be appreciated that the switch S may be provided by solid state switching means, such as thin film transistors on the substrate 36.

FIG. 7 illustrates a further embodiment of the present invention where the sensor can be used as a pH sensor. The structure shown in FIG. 7 is very similar to the structure shown in FIG. 3, so wherever possible like reference numerals have been used to indicate like parts of the structure.

In the structure shown in FIG. 7, a well 58 is provided in the passivation layer 52 to expose the gate electrode 26. The passivation layer 54 is provided extending as a continuous layer over the passivation layer 52 and the gate electrode 26 in the well 58 to provide a relatively thin layer of passivation material 60 overlying the gate electrode. When a sample to be identified in the form of a solution, such as urea or glucose for example, is placed into the well 58 and into contact with the layer 60, ions in the solution are located near to the layer 60 and protons, indicated with + symbols in FIG. 7, are absorbed on surface 62 of layer 60. Because the layer 60 is very thin this charge transfers to the gate electrode 60 and provides therefore a voltage which controls the operation of the TFT transistor constituted by gate electrode 26, polysilicon region 48 and silicon dioxide layer 50. The charge created in the layer 60 by adsorption of the ions onto the surface 62 is related to the pH of the solution deposited into the well 58. Hence, by monitoring the output from the TFT the substance in solution can be identified.

The aforegoing description has been given by way of example only and it will be appreciated by a person skilled in the art that modifications can be made without departing from the scope of the present invention.

For example, the sensor cells have been described with reference to detection of chemical or biomaterials in liquid form. However, it should also be realised that the sensor cells may be used to analyse fluids other than liquids, such as gases.

Furthermore, the present invention has been described with reference to one sensor cell being used to analyse a particular chemical or biomaterial sample. However, as the TFT's can be reliably fabricated into very large area arrays in comparison to silicon substrate devices, the matrix of sensor cells making up the sensor may be provided with several sensor cells, each having a particular DNA string written onto the reference electrode. If such cells are arranged in spaced relationship across the array, the output signals from these sensor cells having a common reference material, such as a DNA string, written onto the reference electrode may be averaged by appropriate circuitry so as to provide enhanced accuracy of analysis. The analysis circuitry may also be fabricated on the substrate using TPT's. Therefore, in essence, the sensor may be provided with a number of 'duplicate' sensor cells, each arranged to identify the common DNA string. This is made possible through the use of TFT's because a very large number of sensor cells can be incorporated into a very large area array.

What is claimed is:

1. A sensor cell comprising a thin film transistor, a reference capacitor coupled to a gate electrode of the thin film transistor, a sample electrode coupled to the gate electrode of the thin film transistor and arranged to receive a sample for identification, the reference capacitor and the sample electrode providing in combination, a capacitance divider circuit coupled to the gate electrode of the thin film transistor, a further transistor for affording a voltage pulse to the gate electrode of the thin film transistor, the voltage pulse having an amplitude arranged to maintain the thin film transistor in a non-conducting condition and to bias the thin film transistor to a point on its operating characteristic where it is ready to switch from the non-conducting condition to a conducting condition; and means for providing an excitation pulse to the gate electrode of the thin film transistor via the capacitance divider circuit, thereby to switch the thin film transistor from the non-conducting condition at the point on its operating characteristic to a conducting condition, whereby in use of the sensor cell, the output current of the thin film transistor is dependent upon the value of capacitance at the sample electrode arising from receiving the sample for identification.

2. A sensor cell comprising a thin film transistor, a sample electrode coupled to the gate electrode of the thin film transistor and arranged to receive a sample for identification, a switching transistor coupled to the gate electrode of the thin film transistor and arranged to switch between a non-conducting condition and a conducting condition to enable a voltage to be selectively provided to the grate electrode of the thin film transistor for selectively switching the thin film transistor between a non-conducting condition and conducting condition, thereby when the switching transistor is switched to the non-conducting condition, the voltage provided at the gate electrode of the thin film transistor is arranged to decrease in magnitude in a time dependent manner and thereby cause the thin film transistor to switch from a conducting to a non-conducting condition, the time taken between the switching of the switching transistor and the switching of the thin film transistor between their respective conducting and non-conducting conditions being dependent upon the value of capacitance at the sample electrode.

3. A method of identifying a sample comprising applying the sample to a sensor cell having a sample electrode arranged in combination with a reference capacitor as a capacitance divider circuit coupled to a gate electrode of a thin film transistor, providing a voltage pulse to the gate electrode of the thin film transistor when in a non-conducting condition, the voltage pulse being arranged to have a magnitude such that the thin film transistor remains in the non-conducting condition and is biased to a point on its operating characteristic where it is ready to switch from the non-conducting condition to a conducting condition, and providing an excitation pulse to the gate electrode of the thin film transistor via the capacitance divider circuit, thereby to switch the thin film transistor from the non-conducting condition at the point on its operating characteristic to the conducting condition, and measuring the output current of the thin film transistor in the conducting condition.

4. A sensor cell as claimed in claim 1, wherein the reference capacitor comprises the gate electrode and a buried region underlaying a metal layer extending into contact with the gate electrode and separated from the metal layer by an insulator layer.

5. A sensor cell as claimed in claim 4, wherein the buried region comprises metal or doped polysilicon.

6. A method as claimed in claim 3, comprising providing the sample electrode in a position offset from the thin film transistor such that the sample is received by the receiving means in a position which does not overlie a gate region of the thin film transistor.

7. A sensor cell as claimed in claim 1, wherein the further transistor comprises a thin film transistor.

8. A method as claimed in claim 3, comprising providing the reference capacitor as a buried region underlying a metal layer extending into contact with the gate electrode and separated from the metal layer by an insulator layer.

9. A sensor cell as claimed in claim 2 comprising a select line for providing a select pulse to a gate electrode of the switching transistor for switching the switching transistor between its conducting and non-conducting conditions.

10. A sensor cell as claimed in claim 9 comprising a preset line for providing the voltage to the gate electrode of the thin film transistor and a read line for providing a read voltage to the thin film transistor, the arrangement being such that a preset cycle is enabled by providing the select pulse to the switching transistor so as to switch the switching transistor to its conducting condition and enable the voltage to be provided to the gate electrode of the thin film transistor, and wherein a read cycle is enabled by terminating the select pulse, thereby the voltage at the gate electrode of the thin film transistor decreases in the time dependent manner in dependence upon the value of capacitance at the sample electrode.

11. A sensor cell as claimed in claim 1, comprising a threshold voltage compensation circuit including a constant current source for providing a preset level of current through the thin film transistor and switching means for selectively coupling the constant current source to the thin film transistor.

12. A sensor cell as claimed in claim 11 comprising an additional transistor coupled to the thin film transistor, the arrangement being such that when the voltage pulse is provided to the gate electrode of the thin film transistor and the constant current source is decoupled from the thin film transistor, the magnitude of an output current from the thin film transistor will change from a first level determined by the constant current source to a second level dependent upon the value of capacitance arising at the sample electrode.

13. A sensor cell as claimed in claim 12 comprising means for determining the change between the first and second levels of the output current from the thin film transistor.

14. A sensor cell as claimed in claim 11, wherein the switching means comprises a thin film transistor switching circuit.

15. A sensor cell as claimed in claim 1, wherein the receiving means comprises gold, silver or platinum.

16. A sensor cell as claimed in claim 1, wherein the receiving means is arranged in a position offset from the thin film transistor, the arrangement being such that the sample is received by the receiving means in a position which does not overlie a gate region of the thin film transistor.

17. A sensor cell as claimed in claim 1, wherein the receiving means comprises a well portion arranged in a passivation layer overlying the thin film transistor thereby to provide a layer of passivation material overlying a metal layer extending into contact with the gate electrode, the layer of passivation material having a thickness such that an electric charge arising in the well portion from receipt by the well portion of the sample for identification creates a voltage at the gate electrode of the thin film transistor indicative of the sample.

18. A sensor cell as claimed in claim 1, wherein the sensor cell comprises a plastics or glass substrate.

19. A sensor comprising an array of rows and columns of sensor cells as claimed in claim 1.

20. A sensor as claimed in claim 19 comprising a row select register for selecting the rows of sensor cells of the array and a column select register for selecting the columns of sensor cells of the array.

21. A sensor as claimed in claim 19 comprising amplification means for amplifying output signals from the sensor cells.

22. A sensor as claimed in claim 19 comprising multiplexing means for multiplexing output signals from the sensor cells.

23. A sensor as claimed in claim 19 comprising storage means for storing reference values indicative of reference samples, comparator means for comparing the reference values with output signals from sensor cells and display means arranged to indicate whether a sample for identification matches a reference sample.

24. A sensor as claimed in claim 19, wherein each sensor cell comprises a reference electrode, and wherein a plurality of reference electrodes disposed in spaced relationship throughout the array are arranged to carry a common reference substance, and the sensor further comprises circuit means for receiving and averaging output signals from those sensor cells including one of the plurality of reference electrodes carrying the common reference substance.

25. A method as claimed in claim 8 comprising providing the buried region as a region of metal or doped polysilicon.

26. A method as claimed in claim 3 comprising providing a threshold voltage compensation circuit including a constant current source for providing a preset level of current through the thin film transistor, and switching means for selectively coupling the constant current source to the thin film transistor.

27. A method as claimed in claim 26 comprising coupling an additional transistor to the thin film transistor, providing the voltage pulse to the gate electrode of the thin film transistor and decoupling the constant current source from the thin film transistor thereby to change the magnitude of the output current from the thin film transistor from a first level determined by the constant current source to a second level dependent upon the value of capacitance arising at the sample electrode.

28. A method as claimed in claim 3, wherein the sample electrode is provided as a well portion arranged in a passivation layer overlying the thin film transistor so as to provide a layer of passivation material overlying a metal layer extending into contact with the gate electrode, the layer passivation material having a thickness such that an electric charge arising in the well portion from receipt by the well portion of the sample for identification creates a voltage at the gate electrode of the thin film transistor indicative of the sample.

29. A method as claimed in claim 3, comprising fabricating the sensor cell on a plastics or a glass substrate.

30. A method as claimed in claim 3 comprising providing a plurality of sensor cells arranged as an array of rows and columns of sensor cells.

31. A method as claimed in claim 30 comprising providing a row select register for selecting the rows of sensor cells in the array and a column select register for selecting the columns of sensor cells of the array.

32. A method as claimed in claim 30 comprising providing amplification means for amplifying output signals from the sensor cells.

33. A method as claimed in claim 30 comprising providing multiplexing means for multiplexing output signals from the sensor cells.

34. A chemical sensor comprising a sensor cell as claimed in claim 1.

35. Fingerprint recognition apparatus comprising a sensor cell as claimed in claim 1.

36. A method of operating a biosensor comprising a method as claimed in claim 3.

37. A method of operating fingerprint recognition apparatus comprising a method as claimed in claim 3.

38. A method of identifying a sample comprising applying the sample to a sensor cell having a sample electrode for receiving the sample, a thin film transistor having a gate electrode coupled to the sample electrode, and a switching transistor coupled to the gate electrode and arranged to switch between a non-conducting and a conducting condition, the method comprising providing a voltage to the gate electrode of the thin film transistor by switching the switching transistor to its conducting condition thereby to place the thin film transistor in a conducting condition, switching the switching transistor from its conducting condition to its non-conducting condition, thereby to cause the voltage provided to the gate electrode of the thin film transistor to decrease in magnitude in a time dependent manner and cause the thin film transistor to switch from the conducting condition to a non-conducting condition, the time taken between the switching of the switching transistor and the switching of the thin film transistor between their respective conducting and non-conducting conditions being dependent upon the value of capacitance at the sample electrode.

39. A method as claimed in claim 38 comprising supplying the switching transistor as a thin film transistor.

40. A method as claimed in claim 38, wherein the switching transistor is switched between the non-conducting and conducting conditions by providing a select pulse from a select line to the switching transistor.

41. A method as claimed in claim 40 comprising providing a preset line for providing the voltage to the gate electrode of the thin film transistor, a read line for providing a read voltage to the thin film transistor, enabling a preset cycle by providing the select pulse to the switching transistor, thereby to switch the switching transistor to a conducting condition to provide the voltage to the gate electrode of the thin film transistor, and enabling a read cycle by terminating the select pulse thereby to switch the switching transistor to the non-conducting condition, whereby the voltage at the gate electrode of the thin film transistor changes in magnitude, thereby to switch the thin film transistor to a non-conducting condition, the time taken between the termination of the select pulse and switching of the thin film transistor to the non-conducting condition being dependent upon the value of capacitance at the sample electrode.

42. A sensor comprising an array of rows and columns of sensor cells as claimed in claim 2.

43. A method as claimed in claim 38 comprising providing a threshold voltage compensation circuit including a constant current source for providing a preset level of current through the thin film transistor, and switching means for selectively coupling the constant current source to the thin film transistor.

44. A method as claimed in claim 38, comprising fabricating the sensor cell on a plastics or a glass substrate.

45. A method as claimed in claim 38, comprising providing a plurality of sensor cells arranged as an array of rows and columns of sensor cells.

46. A chemical sensor comprising a sensor cell as claimed in claim 2.

47. Fingerprint recognition apparatus comprising a sensor cell as claimed in claim 2.

48. A method of operating a biosensor comprising a method as claimed in claim 38.

49. A method of operating fingerprint recognition apparatus comprising a method as claimed in claim 38.

* * * * *